United States Patent
Daavettila et al.

(10) Patent No.: US 10,383,613 B2
(45) Date of Patent: Aug. 20, 2019

(54) STERNAL RETRACTOR WITH RELEASABLE ARMS HAVING CAM LOCKS

(71) Applicant: Scanlan International, Inc., St. Paul, MN (US)

(72) Inventors: Jean E. Daavettila, St. Paul, MN (US); Scott E. Jahns, Hudson, WI (US)

(73) Assignee: Scanlan International, Inc., St. Paul, MN (US)

( * ) Notice: Subject to any disclaimer, the term of this patent is extended or adjusted under 35 U.S.C. 154(b) by 0 days.

(21) Appl. No.: 15/581,523

(22) Filed: Apr. 28, 2017

(65) Prior Publication Data

US 2017/0311940 A1    Nov. 2, 2017

Related U.S. Application Data

(60) Provisional application No. 62/328,748, filed on Apr. 28, 2016.

(51) Int. Cl.
*A61B 17/00* (2006.01)
*A61B 17/02* (2006.01)

(52) U.S. Cl.
CPC .. *A61B 17/0206* (2013.01); *A61B 2017/0092* (2013.01); *A61B 2017/00477* (2013.01)

(58) Field of Classification Search
CPC .............. A61B 17/0206; A61B 17/025; A61B 17/0483; A61B 17/06061; A61B 17/7077; A61B 2017/00477; A61B 2017/00831; A61B 2017/0243; A61B 2017/00243; A61B 2017/00252; A61B 2017/1107; A61B 2017/0256

USPC .................... 600/210–219, 224–235; 606/90
See application file for complete search history.

(56) References Cited

U.S. PATENT DOCUMENTS

| | | | | |
|---|---|---|---|---|
| 2,863,444 A | * | 12/1958 | Winsten ................. | A61B 17/02 600/214 |
| 3,965,890 A | * | 6/1976 | Gauthier ............ | A61B 17/0293 403/79 |
| 4,213,451 A | * | 7/1980 | Swenson .................. | A61B 1/24 600/215 |
| 5,571,072 A | | 11/1996 | Kronner | |

(Continued)

OTHER PUBLICATIONS

Chadwick, Barry and Toto, Chris. "Radiolucent Structural Materials for Medical Applications." Medical Plastics and Biomaterials, Special Section, 23(6), Jun. 2001, 5 pages.

(Continued)

*Primary Examiner* — Pedro Philogene

(57) ABSTRACT

A retractor in accordance with embodiments of the invention includes an adapter and an arm that can be releasably connected to the adapter. An end portion of the arm includes first and second legs and a lock well between the legs. The adapter includes a tubular channel having side walls configured to receive the end portion of the arm, and a lock having a cam in the channel that is rotatable between a release position and a lock position. The lock is configured such that (1) when the lock is in the release position the end portion of the arm can be inserted into the channel and removed from the channel with the cam passing to and from the lock well between the legs, and (2) when the lock is in the lock position the cam is in the lock well and engages the legs to urge the legs into engagement with the side walls of the channel.

31 Claims, 12 Drawing Sheets

(56) References Cited

U.S. PATENT DOCUMENTS

| 5,582,577 | A | * | 12/1996 | Lund | A61B 17/0218 |
| | | | | | 600/204 |
| 6,042,540 | A | | 3/2000 | Johnston et al. | |
| 8,361,153 | B2 | * | 1/2013 | Ralph | A61B 17/025 |
| | | | | | 623/17.11 |
| 2009/0203969 | A1 | * | 8/2009 | Cohen | A61B 17/02 |
| | | | | | 600/245 |

OTHER PUBLICATIONS

Charmant, "Charmant Technology Presentation," Apr. 2016, 8 pages.
Collins, John J. Jr. "Radiolucent Retractor for Operative Coronary Angiography." Department of Surgery, Harvard Medical School and Peter Bent Brigham Hospital, Boston M.A. Accepted for publication Jun. 18, 1976, pp. 478-479.
CTSS. "Cardio-Thoracic Surgery Services: Off-Pumbp Cardiac Surgery." [online]. Retrieved Oct. 18, 2017 using the Internet <http://www.cardiothoracicsurgeryservices.com/21.html>, 2 pages.
Fehling Instruments. "Periling the Difference: Periling Instruments Catalog," pp. 1-56, 2016.
Morgan, Gareth J., et al. "Radiolucent Retractor for Angiographic Analysis During Hybrid Congenital Cardiac Procedures," The Journal of Thoracic and Cardiovascular Surgery, 140(5):1195-1196, Nov. 2010.
Non-Final Office Action issued in U.S. Appl. No. 15/583,705, dated Oct. 1, 2018, 12 pages.
Response to Non-Final Office Action dated Oct. 1, 2018 in U.S. Appl No. 15/583,705, filed Jan. 2, 2019, 23 pages.
Response to Restriction/Election Requirement filed on Aug. 24, 2018, in U.S. Appl. No. 15/583,705, 9 pages.
Restriction/Election Requirement issued in U.S. Appl. No. 15/583,705, dated Jul. 6, 2018, 6 pages.
U.S. Appl. No. 15/583,705, filed May 1, 2017, 44 pages.
U.S. Appl. No. 15/581,680, filed Apr. 28, 2017, 36 pages.

* cited by examiner

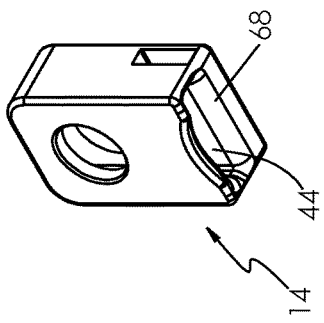
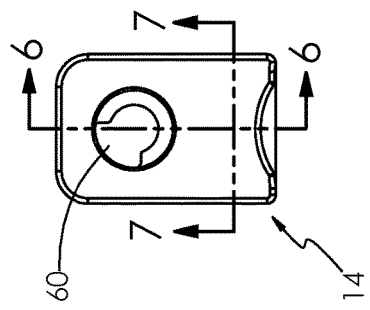
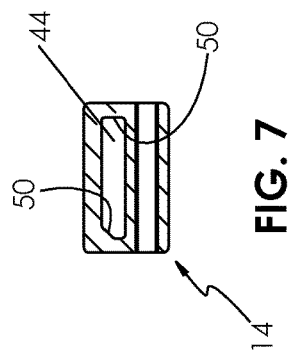
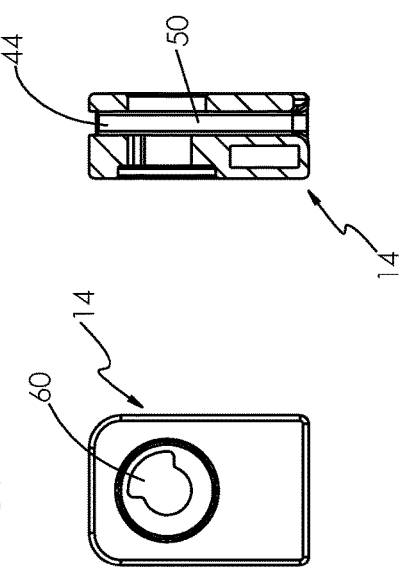

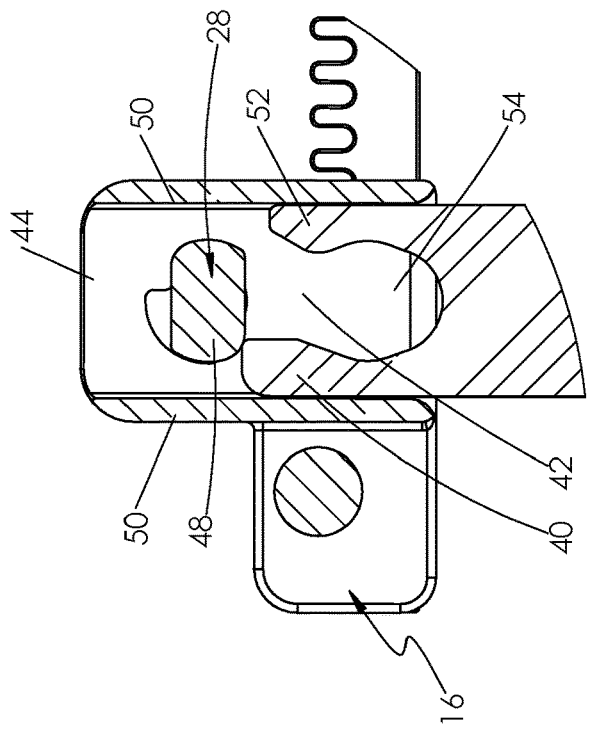
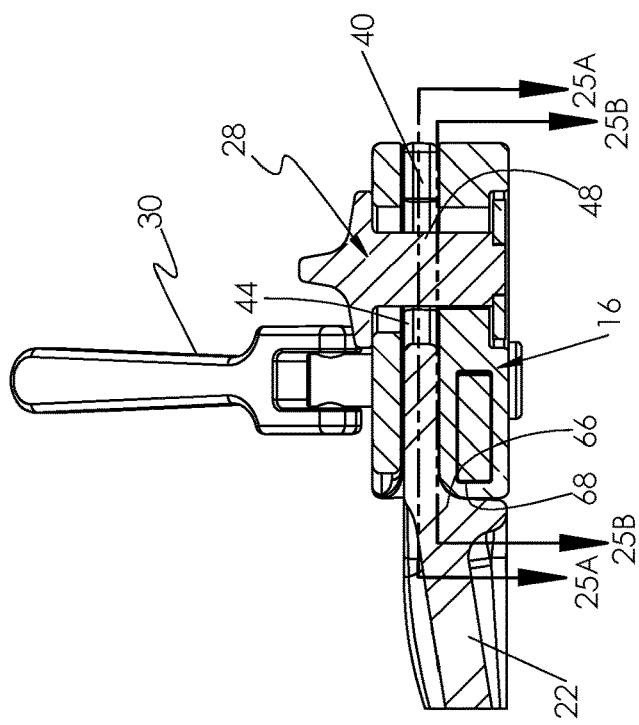

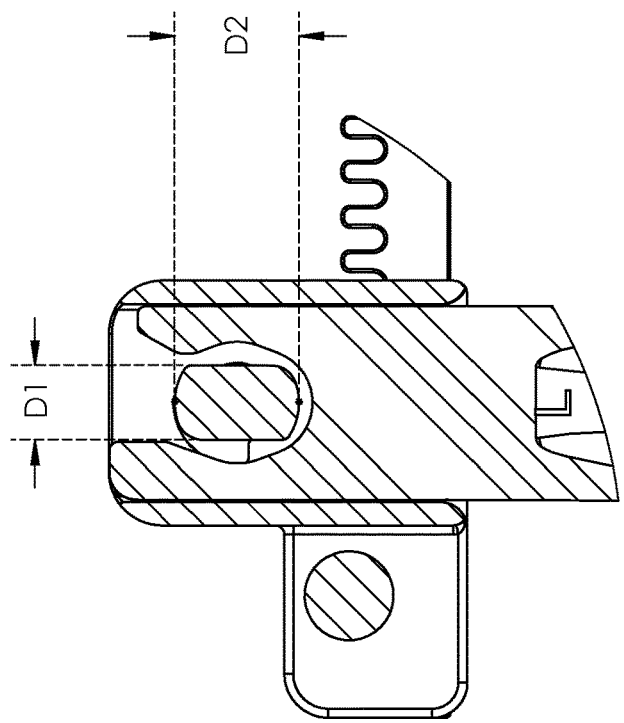
FIG. 25A3
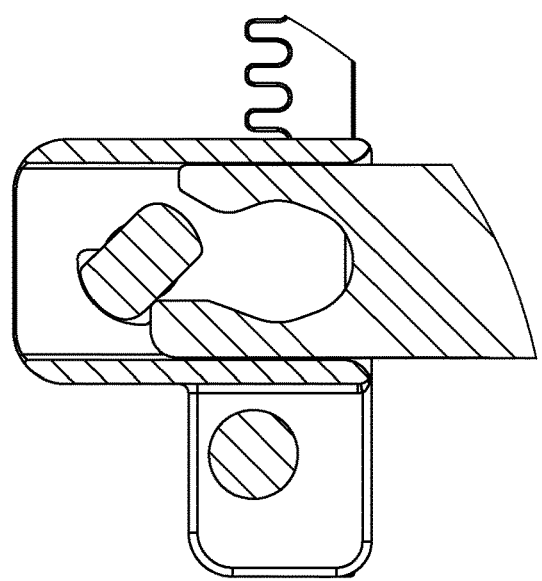
FIG. 25A2

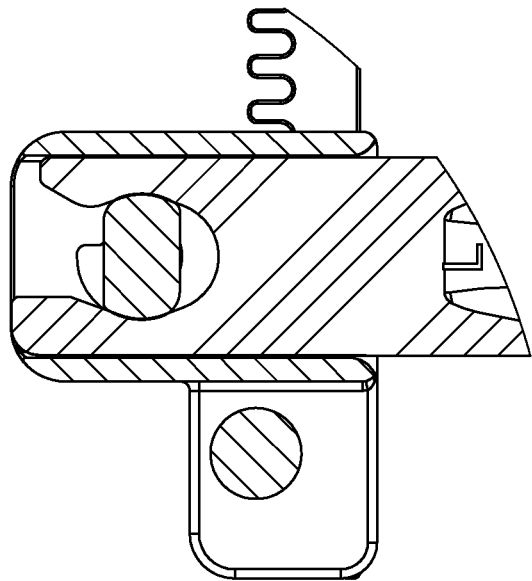
FIG. 25A5
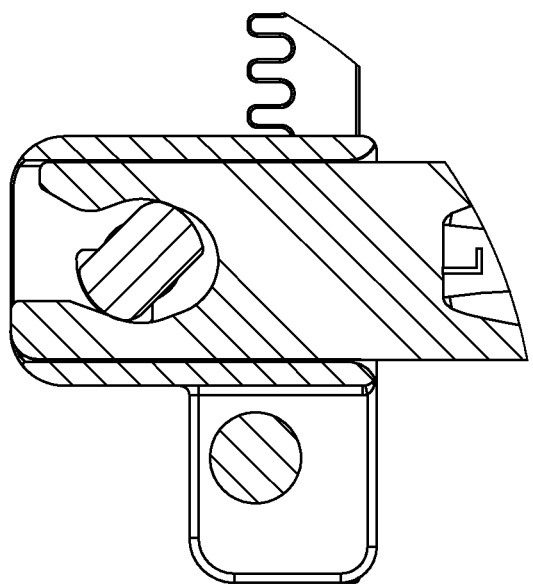
FIG. 25A4

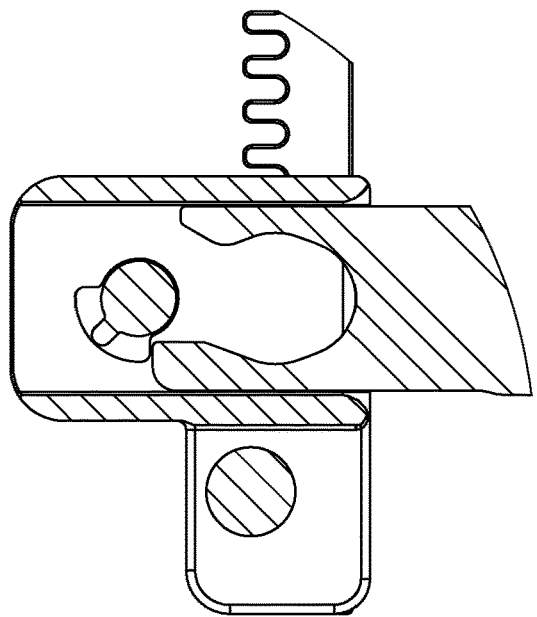
FIG. 25B2
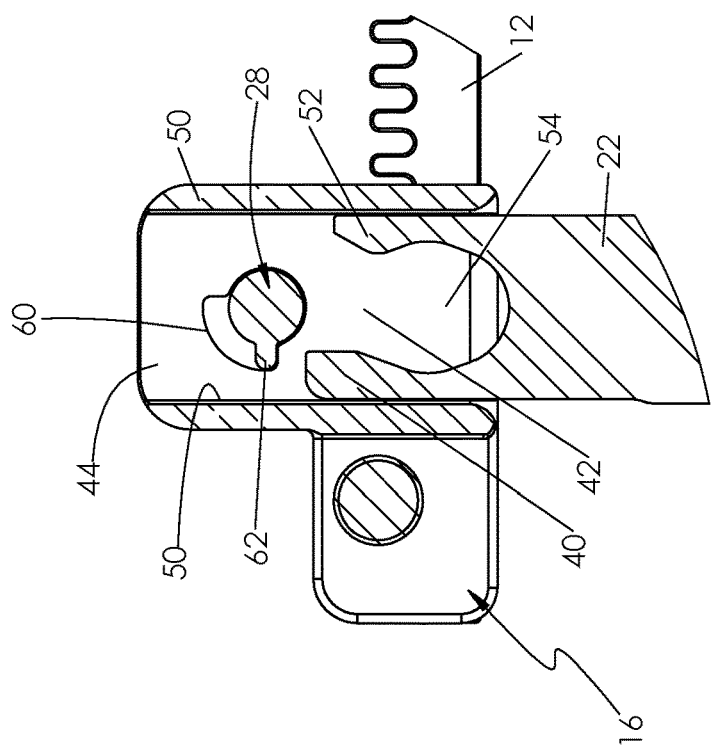
FIG. 25B1

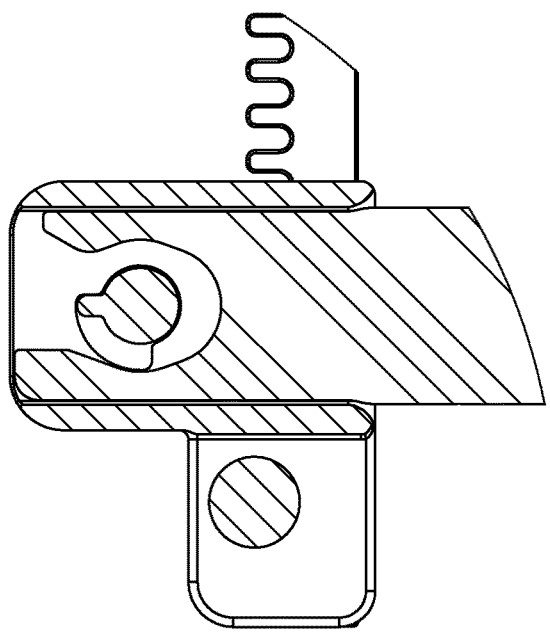
FIG. 25B3
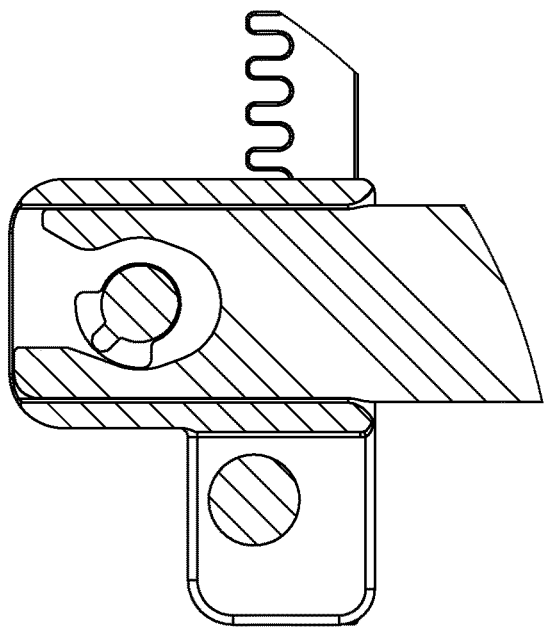
FIG. 25B4

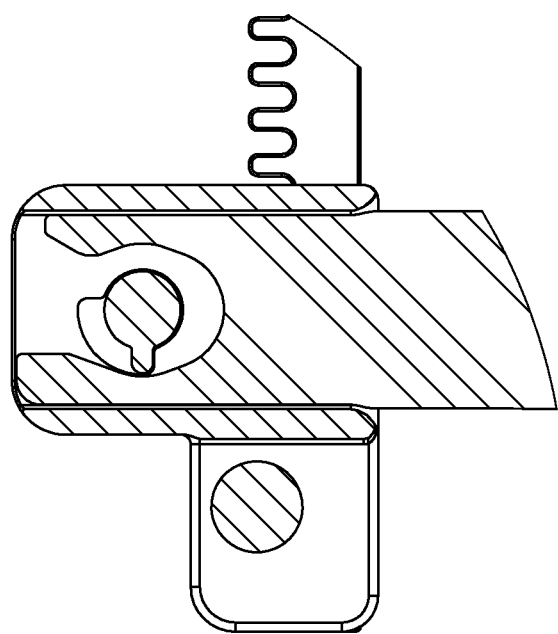
FIG. 25B5

STERNAL RETRACTOR WITH RELEASABLE ARMS HAVING CAM LOCKS

CROSS REFERENCE TO RELATED APPLICATION

This application claims the benefit of U.S. Provisional Application Ser. No. 62/328,748, filed Apr. 28, 2016 and entitled Sternal Retractor with Releasable Arms Having Cam Locks, which is incorporated herein by reference in its entirety and for all purposes.

FIELD OF THE INVENTION

The invention relates generally to surgical instruments. In particular, embodiments of the invention include sternal and other retractors.

BACKGROUND

Surgical devices such as sternal and other retractors are generally known and commercially available. Devices of these types are often made from metal such as stainless steel or titanium. Materials of these types can block the transmission of x-rays and thereby interfere with or prevent the imaging of anatomical features near the devices. Materials that inhibit the passage of imaging electromagnetic radiation are sometimes called radiodense.

During complex surgical procedures, surgeons often perform radiographic imaging to determine the anatomical and physiological state of the patient. Removing a metal retractor to allow for imaging during such a surgical procedure may take time and disturb the procedure, thereby increasing the risk of complications. Materials that allow the transmission of imaging electromagnetic radiation are sometimes called radiolucent.

There remains a continuing need for improved surgical retractors. In particular, there is a need for retractors that are radiolucent at the surgical site. Any such retractors should be highly functional and capable of being efficiently used.

SUMMARY

An improved retractor in accordance with embodiments of the invention has an adapter and an arm that are configured to be releasably connected. The retractor includes a first connector structure on one of the adapter and the arm and a second connector structure on the other of the adapter and the arm. The first connector structure includes an end portion having at least a first leg, and a lock well adjacent each leg. The second connector structure includes a channel configured to receive the end portion of the first connector structure, including each leg, at an inserted position, and a lock in the channel that is movable between a release position and a lock position. The lock is configured such that (1) when the lock is in the release position the end portion of the first connector structure can be inserted into the channel to the inserted position and removed from the channel, and (2) when the lock is in the lock position the lock engages at least the first leg to resist withdrawal of the end portion of the first connector structure from the channel.

In embodiments, the lock includes a cam that is rotatably mounted to the second connector structure, and that rotates between the release and lock positions. The channel of the second connector structure includes a side wall, and when the cam is in the lock position the cam urges the first leg into engagement with the side wall of the channel.

In embodiments, the end portion of the first connector structure includes first and second legs, and the lock well is between the first and second legs. The lock is configured such that (1) when the lock is in the release position the end portion of the first connector structure can be inserted into the channel to the inserted position and removed from the channel with the lock in the lock well between the first and second legs, and (2) when the lock is in the lock position the lock engages the first and second legs to resist withdrawal of the legs from the channel. The channel can include first and second side walls, and when the lock is in the lock position the lock urges the first and second legs into engagement with the side walls of the channel.

In embodiments, the first and second connector structures are configured such that during insertion of the end portion of the first connector structure a leg will engage the lock if the lock is in the lock position, and move the lock toward the release position. The first leg can be longer than the second leg, and the first leg will engage the lock if the lock is in the lock position during insertion of the end portion of the first connector structure, and move the lock toward the release position.

BRIEF DESCRIPTION OF THE DRAWINGS

FIG. 3 is an isometric view of the stationary adapter shown in FIG. 1, illustrating a first side of the adapter.

FIG. 4 is a side view of the stationary adapter shown in FIG. 3, illustrating a second side opposite the side shown in FIG. 3.

FIG. 5 is a side view of the stationary adapter shown in FIG. 3, illustrating the first side of the adapter shown in FIG. 3.

FIG. 6 is a sectional view of the adapter shown in FIG. 5, taken along line 6-6 in FIG. 5.

FIG. 7 is a sectional view of the adapter shown in FIG. 5, taken along line 7-7 in FIG. 5.

FIG. 24 is a detailed sectional end view of the retractor shown in FIG. 1, illustrating the end with the moving adapter and arm.

FIGS. 25A1-25A5 are detailed cross sectional views of the moving adapter, arm and lock taken along line 25A-25A in FIG. 24, illustrating the end of the arm at a sequence of positions during insertion into the adapter, and the position of the cam of the lock at each arm position.

FIGS. 25B1-25B5 are detailed cross sectional views of the moving adapter, arm and lock taken along line 25B-25B in FIG. 24, illustrating the end of the arm at the sequence of positions during insertion into the adapter shown in FIGS. 25A1-25A5, and the position of the tab of the lock at each arm position.

DETAILED DESCRIPTION

Figure 1:
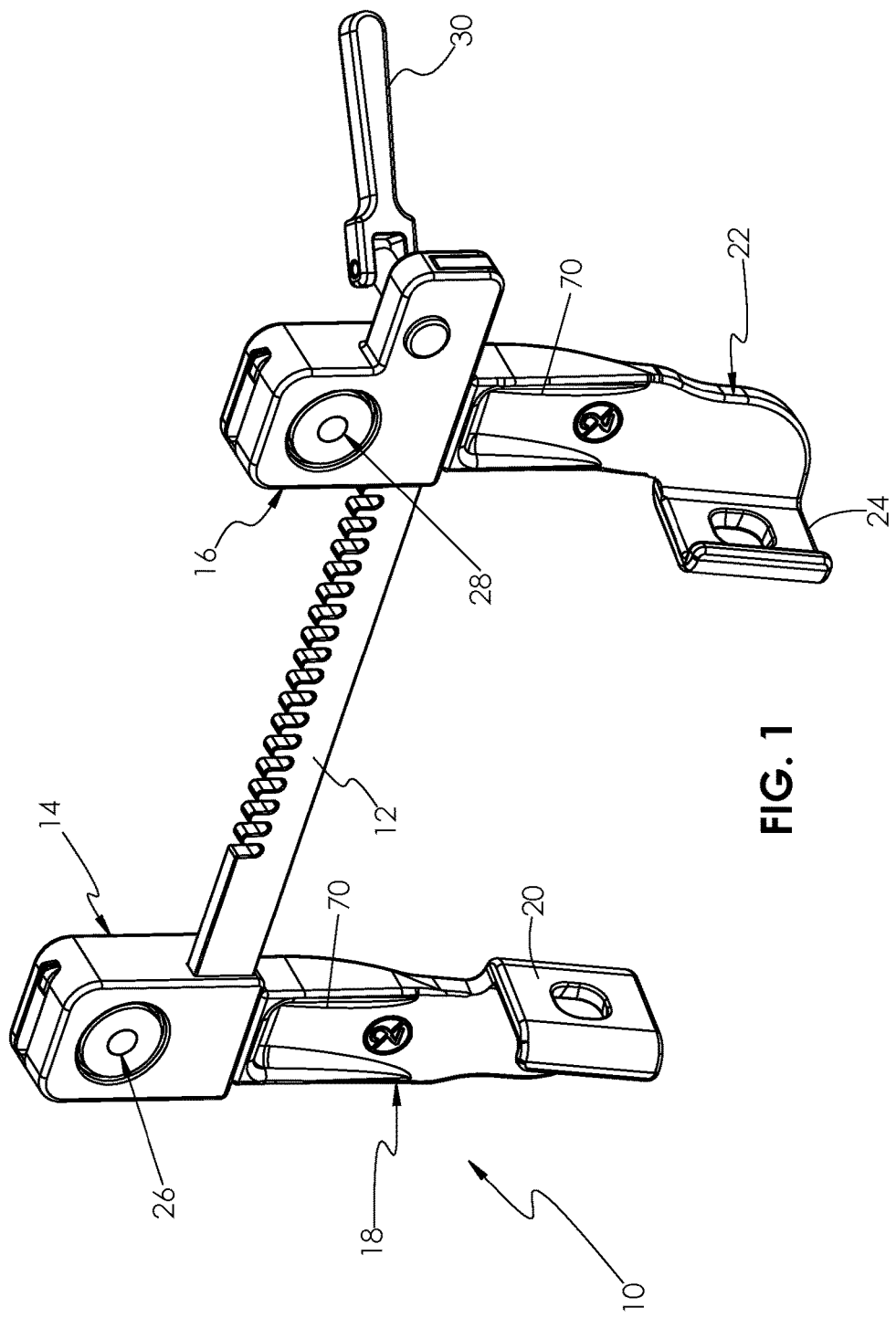
FIG. 1 is an isometric view of a sternal tissue/bone retractor in accordance with embodiments of the invention.
Figure 2:
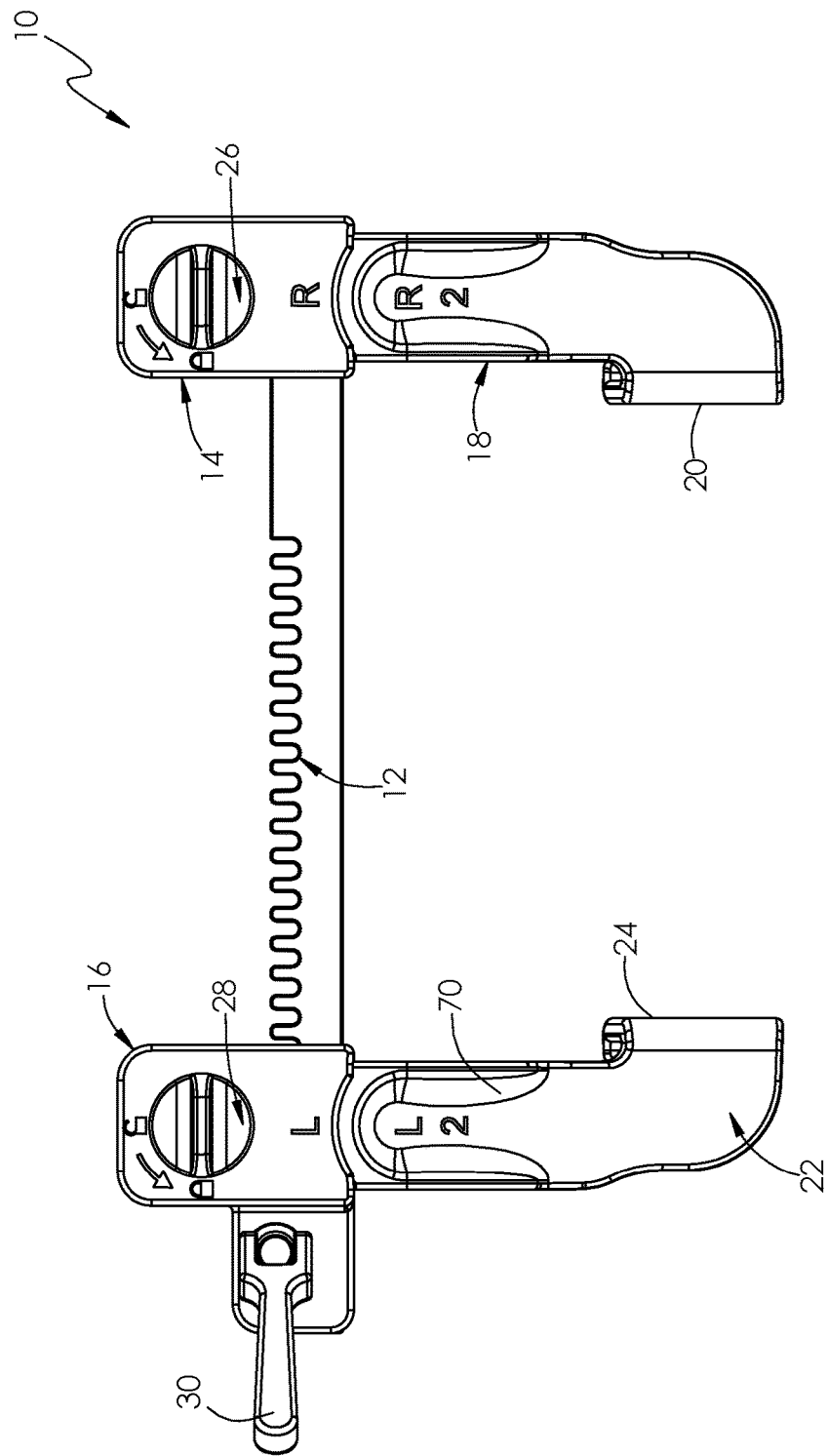
FIG. 2 is a plan view of the retractor shown in FIG. 1, illustrating the side of the retractor opposite the side shown in FIG. 1.
Figure 8:
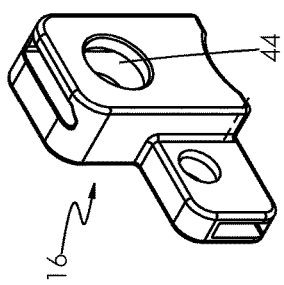
FIG. 8 is an isometric view of the moving adapter shown in FIG. 1, illustrating a first side and first end of the adapter.
Figure 9:
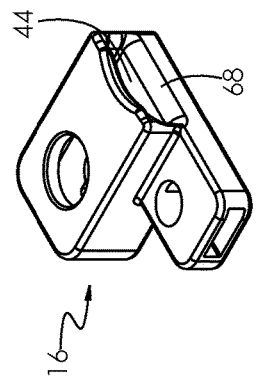
FIG. 9 is an isometric view of the moving adapter shown in FIG. 8, illustrating the first side and a second end opposite the end shown in FIG. 8.
Figure 12:
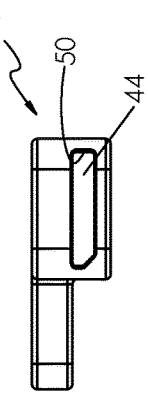
FIG. 12 is an end view of the adapter shown in FIG. 8, illustrating the first end shown in FIG. 8.
Figure 11:
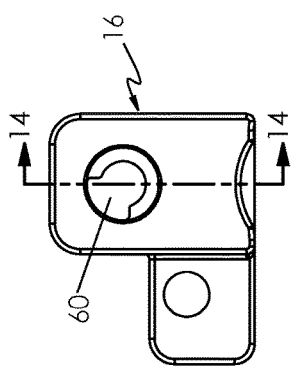
FIG. 11 is a side view of the adapter shown in FIG. 8, illustrating the first side of the adapter shown in FIG. 8.
Figure 13:
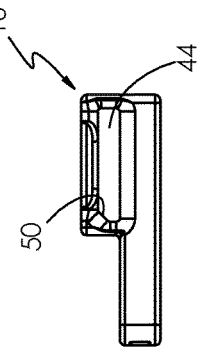
FIG. 13 is an end view of the adapter shown in FIG. 8, illustrating the second end shown in FIG. 9.
Figure 14:
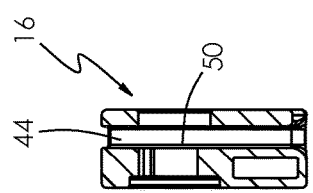
FIG. 14 is a sectional view of the adapter shown in FIG. 11, taken along line 14-14 in FIG. 11.
Figure 10:
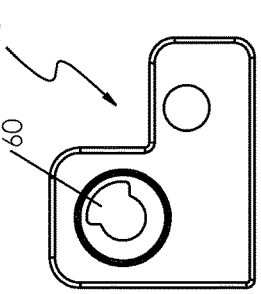
FIG. 10 is a side view of the adapter shown in FIG. 8, illustrating a second side opposite the side shown in FIG. 8.

A sternal retractor 10 in accordance with embodiments of the invention can be described generally with reference to FIGS. 1 and 2. As shown, the retractor 10 includes a rack 12, stationary adapter block or adapter 14, movable adapter block or adapter 16, first (e.g., right) arm 18 having a blade 20, second (e.g., left) arm 22 having a blade 24, locks 26 and 28, and crank 30. Stationary adapter 14 is generally fixedly mounted to one end of the rack 12, and the movable adapter 16 is movably attached to the rack between the opposite end and the stationary adapter. As described in greater detail below, during use of the retractor 10 the arms 18 and 22 (which can be metal such as titanium or high density polymers) can be selected from sets of differently sized and packaged sterilized arms, removed from the packaging, and inserted into the adapters 14 and 16, respectively. The locks 26 and 28 are then actuated to lock or securably engage the arms 18 and 22 to the adapters 14 and 16, respectively. During surgical procedures, the crank 30 of retractor 10 can be actuated to move the movable adapter 16 and arm 22 attached thereto with respect to the stationary adapter 14 and arm 20. After the use of the retractor 10, the locks 26 and 28 can be actuated to release the arms 18 and 22, and the arms can be removed from the adapters 14 and 16, respectively. The previously used arms 18 and 22 can be disposed of or sterilized and repackaged for another use.

Other features of retractors 10 in accordance with embodiments of the invention can be described with reference to FIGS. 1-25. The retractor 10 has adapters 14 and/or 16 and arms 18 and/or 22 that are configured to be releasably connected. A first connector structure is on one of the adapter 14 and/or 16 and the arm 18 and/or 22. In the illustrated embodiment (e.g., FIGS. 15-18) the first connector structure includes an end portion on the arms 18 and/or 22 having at least a first leg 40 and a lock well 42 adjacent each leg. A second connector structure is on the other of the adapter 14 and/or 16 and the arm 18 and/or 22. In the illustrated embodiment (e.g., FIGS. 3, 6-9, and 12-14) the second connector structure includes a tubular portion of the adapters 14 and/or 16 that define a channel 44 in each adapter. The channel 44 of each adapter 14 and/or 16 is configured to receive the end portion of the first connector structure, including each leg 40 of arms 18 and/or 22, at an inserted position. The second connector structures also include the locks 26 and/or 28 in the channels 44 of the adapters 14 and/or 16 (e.g., FIGS. 24, 25A1-25A5 and 25B1-25B5). Each of the locks 26 and/or 28 is movable between a release position and a lock position (e.g., FIGS. 25A1-25A5 and 25B1-25B5). Each of locks 26 and/or 28 is configured such that (1) when the lock is in the release position (e.g., FIGS. 25A1 and 25A3) the end portion of the associated leg 40 of arms 18 and/or 22 (i.e., the first connector structure) can be inserted into the channel 44 to the inserted position and removed from the channel, and (2) when the lock is in the lock position (e.g., FIG. 25A5) the lock engages at least the first leg to resist withdrawal of the end portion of the arm from the channel.

In the illustrated embodiment, the locks 26 and/or 28 include a cam 48 that is rotatably mounted to the adapters 14 and/or 16 (i.e., the second connector structures) and that rotates between the release and lock positions. The channels 44 of the adapters 14 and/or 16 include side walls 50, and when the cams 48 are in the lock positions the cams urge the first legs 40 into engagement with the side walls of the channels.

The end portion of the arms 18 and/or 22 (i.e., the first connector structures) include first and second legs 40 and 52, respectively, in the illustrated embodiments. As shown, the lock well 42 is between the first and second legs 40 and 52, and each lock 26 and/or 28 is configured such that (1) when the lock is in the release position the legs 40 and 52 (i.e., the end portion of the first connector structure) can be inserted into the channel 44 to the inserted position and removed from the channel with the cam 48 of the lock in the lock well between the first and second legs (e.g., FIGS. 25A1 and 25A3), and (2) when the lock is in the lock position the lock engages the first and second legs, and urges the first and second legs into engagement with the side walls 50 of the channel, to resist withdrawal of the legs from the channel (e.g., FIG. 25A5).

In the illustrated embodiments, each lock well 42 includes a lock seat 54. The cams 48 of the locks 26 and/or 28 are in the lock seats 54 when the first and second legs 40 and 52 are in the inserted position. As shown, the lock well 42 includes an opening region between distal ends of the legs 40 and 52 at the end portion of each arm 18 and/or 22. The opening region is characterized by a first distance between the first and second legs 40 and 52. The lock seat 54 is proximal to the opening region and is characterized by a second distance between the first and second legs 40 and 52, and the second distance is greater than the first distance. The cam 48 of each lock 26 and/or 28 has a first diameter D1 and a second diameter D2 (e.g., FIGS. 20, 21 and 25A3). The first diameter of the cam 48 is less than the first distance of the opening region of the lock well 42, such that when each lock 26 and/or 28 is in the release position the lock can pass between the first and second legs 40 and 52 and into the lock seat 54 when the end portion of the arm 18 and/or 24 is inserted into and removed from the channel 44 (e.g., FIGS. 25A1-25A3). The second diameter of the cam 48 is greater than the first distance of the opening region of the lock seat 54, and optionally greater than the second distance of the lock seat. As shown, the locks 26 and/or 28 include cams 48 mounted to the associated adapter 14 and/or 16 for rotation within the channels 44. A knob 56 is connected to the cam 48 to enable a user to rotate the locks 26 and/or 28 between the release and lock positions.

Embodiments of the retractor 10 also include a stop structure in one or both of the adapters 14 and/or 16 (i.e., the second connector structures) and the arms 18 and/or 22 (i.e., the first connector structures) to constrain motion of the locks 26 and/or 28 between the release and lock positions. In the illustrated embodiments the stop structure includes a stop opening 60 in the adapters 14 and/or 16 and a tab 62 connected to the locks 26 and/or 28 that extends into the stop opening. The tab 62 moves within the stop opening 60 of each adapter 14 and/or 16 and engages the adapter at the release position (e.g., FIG. 25B3) and the lock position (e.g., FIG. 25B5). The stop openings 60 and tabs 62 are configured such that the release and lock positions are located at ends of a rotational lock travel path of about 90° in the illustrated embodiments.

In embodiments of the retractor 10, the adapters 14 and/or 16 (i.e., the second connector structure) and arms 18 and/or 22 (i.e., the first connector structure) are configured such that during insertion of the end portion of a leg such as 40 of an arm, the leg will engage the lock 26 and/or 28 if the lock is in the lock position, and move the cam 48 of the lock toward the release position (i.e., the first connector structure can be inserted into the second connector structure when the lock is in the lock position) (e.g. FIGS. 25B1-25B3 and 25A1-25A3). In the illustrated embodiments the first leg 40 is longer than the second leg 52. The first leg 40 will engage the cam 48 of the lock 26 and/or 28 if the lock is in the lock position during insertion of the end portion of an arm 18 and/or 22, and move the lock toward the release position. As shown, the locks 26 and/or 28 are mounted to the associated adapters 14 and/or 16 for rotation within the channels 44 between the release and lock positions about a rotational axis that is between the first and second legs 40 and 52. The first leg 40 will engage the cam 48 of the lock 26 and/or 28 if the lock is in the lock position during insertion of the end portion of the arm 18 and/or 22, and rotate the lock toward the release position. Each lock seat 54 is generally elliptically-shaped in the illustrated embodiments (e.g., FIGS. 25A1 and 25B1).

Figure 15:
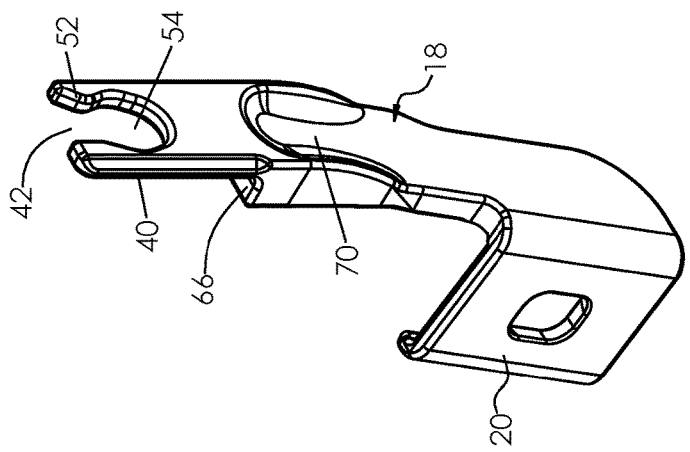
FIG. 15 is an isometric view of the stationary or right side-arm shown in FIG. 1, illustrating a first side of the arm and a first side of a blade on the arm.
Figure 17:
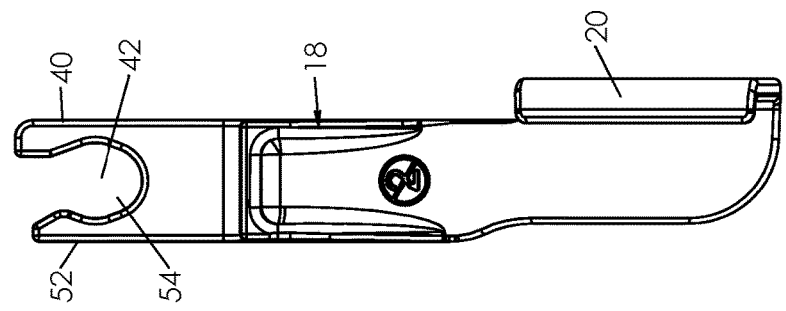
FIG. 17 is a side view of the arm shown in FIG. 15, illustrating a second side opposite the side shown in FIG. 15.
Figure 18:
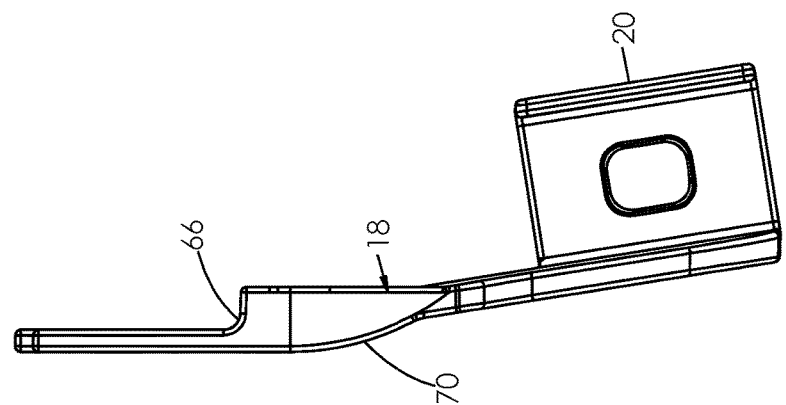
FIG. 18 is an edge view of the arm shown in FIG. 15, illustrating a second side of the blade opposite the side shown in FIG. 15.

The end portion of each arm 18 and/or 22 extends from a shoulder 66 in the illustrated embodiments (e.g., FIGS. 15, 18 and 24). Each adapter 14 and/or 16 includes an edge 68 that is engaged by the shoulder 66 of the associated arm 18 and/or 22 when the arm is in the inserted position (e.g., FIGS. 3, 9 and 24). Each arm 18 and/or 22 can also include a gusset 70 on a portion of the arm adjacent to the shoulder (e.g., FIGS. 15 and 16).

Although illustrated and described above in connection with a sternal retractor, in other embodiments the first connector structure is on the end of other retractor arms such as a self-retaining retractor arm, or a spinal retractor arm (e.g., a so-called Adson retractor). The retractor arms such as 18 and/or 22 can include (1) only radiolucent material, (2) only radiodense material, or (3) both of radiolucent and radiodense material. Similarly, the adapters 14 and/or 16 can include (1) only radiolucent material, (2) only radiodense material, or (3) both of radiolucent and radiodense material. As noted above, embodiments of the invention include packaged sterile retractor arms such as 18 and/or 22 having first or second connector structures of the types described above, and optionally different types (e.g., left and right) and sizes of such arms. Similarly, embodiments include packaged sterile retractor adapters such as 14 and/or 16 having the first or second connector structures of the types described above, and optionally different types (e.g., left and right) of such adapters.

Embodiments of the invention offer important advantages. They can, for example, allow x-ray and other imaging of target tissues. They incorporate the use of metals outside of the target, thereby providing strength, reuse and other high-quality functionality. The ability to efficiently attach and detach various sizes and configurations of arms and blades offers efficiencies by saving the surgeon time and providing optimal fitting to the patient and procedural needs. For example, the device can be configured for pediatric, adolescent and adult patients. The retractors can accommodate both radiolucent (e.g., polymer) and radiodense (e.g., titanium, stainless steel) arms and blades.

During operation, following removal of the sterile left arm 22 and right arm 18 from the packaging (not shown) the operating room (OR) staff will insert the arms into the movable adapter 16 and stationary adapter 14. The locks 26 and 28 do not have to be in any particular position for insertion of the arms 22 or 18. Because of the configuration of the interface between the arms 22 and 18, the leading leg 40 will hit either the flat surface or the radiused surface of the cam 48 of locks 28 and/or 26, and cause the lock and cam to rotate to the "open" position. Since the leading leg 40 hits the cam 48 at the furthest point from the center of the shaft, it causes a torque about the lock 28 and/or 26, thereby rotating the lock to the open position. FIG. 25A3 shows the cam 48 in the "open" position, and FIG. 25A5 shows the cam in the "closed" position.

The rotation of the locks 28 and/or 26 is limited by the tabs 62. A tab 62, shown in FIGS. 25B1-25B5 on the bottom of the cam 48 engages in stop opening 60, thereby providing 90° degrees of rotation. The "open" position being at 90° (e.g., FIG. 25B3) and the "closed" or "locked" position being parallel with the rack 12 (e.g., FIG. 25B5). This feature will save confusion when the OR staff loads the arms 18 and/or 22, which in turn should make training easier and save time in the OR.

Once the arm 18 and/or 22 is fully inserted, the torque shoulder 66 of the arm will rest against the front face or edge 68 of the associated adapter 14 and/or 16. When force is applied to an arm 18 and/or 22, the arm will create a torque about the associated lock 26 and/or 28, placing a load upon the leading leg 40 and the trailing leg 52 and the mating surfaces of the adapter. The step in the arm was so designed to create the torque shoulder 66 to help reduce the force on the two legs 40 and 52.

With an arm 18 and/or 22 abutted to the associated adapter 14 and/or 16 front face, the arm can be locked into place. The OR staff will rotate the lock 26 and/or 28 ninety degrees counter clock wise. Graphics (not shown) can be included on the adapter 14 and/or 16 to provide visual ques.

When the lock 26 and/or 28 reaches full rotation the tab 62 on the lock will hit the surface that defines the stop opening 60, stopping it. At this position the cam 48 will apply a force to the cam lock seat 54, and the force will spread the legs 40 and 52 slightly to take up any clearance between the adapter 14 and/or 16 housing and the legs. This provides a nice engaged feel to the OR staff and prevents the arm 18 and/or 22 from wiggling during handling.

The cam lock seat 54 is not a perfectly round feature (e.g., FIGS. 16, 17, 25A1) in embodiments. Instead, it has two seat locations that correspond to the closed or lock position of the locks 26 and/or 28. These seat 54 features and flex of the legs 40 and/or 52 assure that a deliberate torque force must be applied to the locks 26 and/or 28 to "unlock" the arms.

Figure 16:
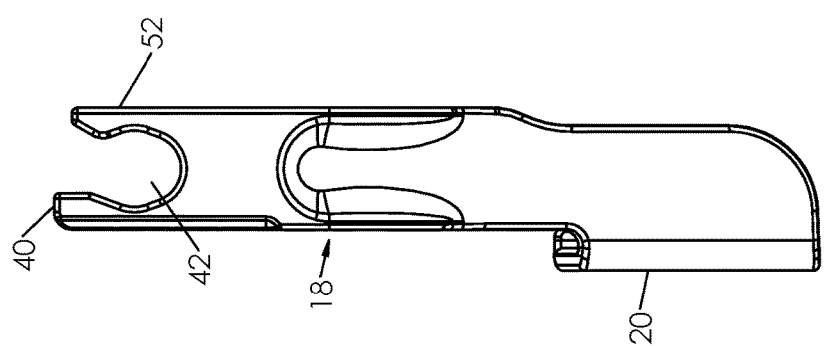
FIG. 16 is a side view of the arm shown in FIG. 15, illustrating the first side shown in FIG. 15.
Figure 19:
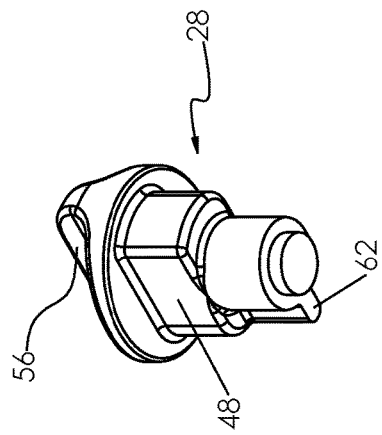
FIG. 19 is an isometric view of the lock shown in FIG. 1.
Figure 20:
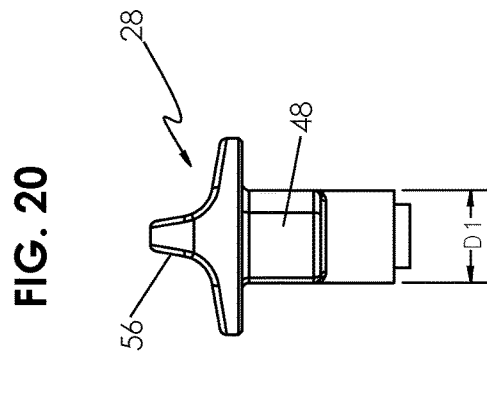
FIG. 20 is a side view of the lock shown in FIG. 19.
Figure 22:
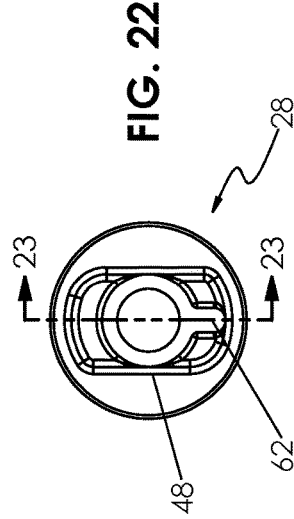
FIG. 22 is an end view of the lock shown in FIG. 19, illustrating the end shown in FIG. 19.
Figure 21:
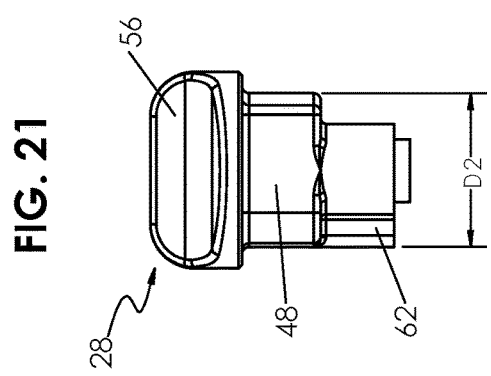
FIG. 21 is a side view of the lock shown in FIG. 19, illustrating a side offset from the side shown in FIG. 20 by 90°.
Figure 23:
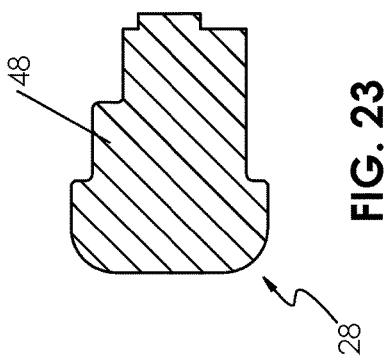
FIG. 23 is a sectional view of the lock shown in FIG. 19, taken along line 23-23 in FIG. 22.

The gusset 70 (e.g., FIG. 16, showing top view of arm 18) was integrated into the arm design based on Finite Element Analysis (FEA) to optimize the strength of the arm and to reduce torque about the arm as the blades 20 and/or 24 engage the sternum or other anatomical structures. Similar integrated gussets are incorporated in the bottom of the arms 18 and/or 22 (e.g., FIG. 17) in embodiments.

An advantage of embodiments of the retractor 10 is that it can accommodate titanium arms 18 and/or 22. Titanium has considerable resilience and can handle the slight spreading of the legs 40 and/or 52. The use of Titanium also provides other advantages. One is to produce a light retractor for use on pediatric patients. Another is that it is generally safe for use in an MRI imagining machine. This design not only allows for radiographic imaging in the areas of the arms but may also be used with MRI imaging technologies.

Another important feature of embodiments of retractor 10 is the feature integrated into the adapters 14 and/or 16. This prevents the user from accidentally inserting the left arm 22 into the right adapter 14. The key feature was created which prevents the arm from even starting into the adapter housing.

Although the invention is described with reference to preferred embodiments, those of skill in the art will recognize that changes can be made in form and detail without departing from the spirit and scope of the invention.

What is claimed is:
1. A retractor, comprising:
a retractor adapter;
a retractor arm releasably connectable to the retractor adapter:
a first connector structure on one of the retractor adapter and the retractor arm, the first connector structure including:
an end portion having at least a first leg; and
a lock well adjacent each leg; and
a second connector structure on the other of the retractor adapter and the retractor arm, the second connector structure including:
a channel configured to receive the end portion of the first connector structure, including each leg, at an inserted position; and
a lock in the channel that is movable between a release position and a lock position, wherein the lock is configured such that (1) when the lock is in the release position the end portion of the first connector structure can be inserted into the channel to the inserted position and removed from the channel, and (2) when the lock is in the lock position the lock engages at least the first leg to resist withdrawal of the end portion of the first connector structure from the channel.
2. The retractor of claim 1 wherein the lock includes a cam that is rotatably mounted to the second connector structure and that rotates between the release and lock positions.
3. The retractor of claim 2 wherein:
the channel of the second connector structure includes a side wall; and
wherein when the cam is in the lock position the cam urges the first leg into engagement with the side wall of the channel.
4. The retractor of claim 1 wherein:
the end portion of the first connector structure includes first and second legs;
the lock well is between the first and second legs; and
a lock is configured such that (1) when the lock is in the release position the end portion of the first connector structure can be inserted into the channel to the inserted position and removed from the channel with the lock in the lock well between the first and second legs, and (2) when the lock is in the lock position the lock engages the first and second legs to resist withdrawal of the legs from the channel.
5. The retractor of claim 4 wherein:
the channel includes first and second side walls; and
wherein when the lock is in the lock position the lock urges the first and second legs into engagement with the side walls of the channel.
6. The retractor of claim 5 wherein:
the lock well includes a lock seat; and
the lock is in the lock seat when the first and second legs are in the inserted position.
7. The retractor of claim 6 wherein:
the lock well includes an opening region between distal ends of the legs at the end portion of the first connector structure, and wherein the opening region is characterized by a first distance between the first and second legs;
the lock seat is proximal to the opening region and is characterized by a second distance between the first and second legs, and wherein the second distance is greater than the first distance; and
the lock has first and second diameters, wherein (1) the first diameter is less than the first distance of the opening region of the lock well, such that when the lock is in the release position the lock can pass between the first and second legs and into the lock seat when the end portion of the first connector structure is inserted into and removed from the channel, and (2) the second diameter is greater than the first distance of the opening region of the lock seat, and optionally greater than the second distance of the lock seat.
8. The retractor of claim 1 wherein the lock is a cam mounted to the second connector structure for rotation within the channel.
9. The retractor of claim 8 and further including a knob connected to the cam to enable a user to rotate the cam between the release and lock positions.
10. The retractor of claim 1 and further including stop structure in one or both of the first and second connector structures to constrain motion of the lock between the release and lock positions.
11. The retractor of claim 10 wherein the stop structure includes:
a stop opening in the second connector structure; and
a tab connected to the lock and extending into the stop opening.
12. The retractor of claim 11 wherein:
the lock is mounted to the second connector structure for rotation between the release and lock positions; and
the tab moves within the stop opening of second connector structure and engages the second connector structure at the release and lock positions.
13. The retractor of claim 12 wherein stop opening and tab are configured such that the release and lock positions are located at ends of a rotational lock travel path of about 45°.
14. The retractor of claim 1 wherein the first and second connector structures are configured such that during insertion of the end portion of the first connector structure a leg will engage the lock if the lock is in the lock position, and move the lock toward the release position.
15. The retractor of claim 4 wherein:
the first leg is longer than the second leg; and
the first leg will engage the lock if the lock is in the lock position during insertion of the end portion of the first connector structure, and move the lock toward the release position.

16. The retractor of claim 15 wherein:
the lock is mounted to the second connector structure for rotation within the channel between the release and lock positions about a rotational axis that is between the first and second legs; and
the first leg will engage the lock if the lock is in the lock position during insertion of the end portion of the first connector structure, and rotate the lock toward the release position.

17. The retractor of claim 16 wherein the lock well is generally elliptically-shaped.

18. The retractor of claim 1 wherein the lock includes a cam having at least first and second different diameters.

19. The retractor of claim 1 wherein the second connector structure includes a tubular structure defining the channel.

20. The retractor of claim 1 wherein:
the end portion of the first connector structure extends from a shoulder; and
the second connector structure includes an edge that is engaged by the shoulder of the first connector structure when the first connector structure is in the inserted position.

21. The retractor of claim 20 and further including a gusset on a portion of the first connector structure adjacent to the shoulder.

22. The retractor of claim 1 wherein the first connector structure is on an end of a retractor arm, optionally on an end of a sternal retractor arm, a self-retaining retractor arm, or a spinal retractor arm.

23. The retractor of claim 22 wherein the retractor arm includes (1) only radiolucent material, (2) only radiodense material, or (3) both of radiolucent and radiodense material.

24. The retractor of claim 23 wherein the second connector structure includes (1) only radiolucent material, (2) only radiodense material, or (3) both of radiolucent and radiodense material.

25. A surgical retractor arm comprising:
a proximal end portion configured for attachment to a retractor adapter, including:
first and second retractor component legs including ends; and
a lock well between the first and second legs configured to receive a rotating cam lock rotatable between release and locked positions, the lock well including:
an opening region between the ends of the legs, wherein the opening region is characterized by a first distance between the first and second legs; and
a lock seat distal to the opening region, wherein the lock seat is characterized by a second distance between the first and second legs, and wherein the second distance is greater than the first distance, such that when the cam lock is in the release position the cam lock can pass between the first and second legs and into the lock seat, and when the cam lock is in the locked position the cam lock engages the first and second legs; and
a distal end portion including a retractor blade.

26. The retractor arm of claim 25 wherein the component is a polymer retractor arm.

27. The retractor arm of claim 26 wherein the first leg is longer than the second leg, and the first leg will engage the cam lock if the cam lock is in the lock position and move the cam lock toward the release position.

28. The retractor arm of claim 27 wherein the lock well is generally elliptically shaped.

29. A first component for a surgical retractor, wherein the first component is configured to receive an end portion of a second component having at least a first leg and a lock well adjacent each leg, the first component comprising:
a retractor channel configured to receive the end portion of the second component, including each leg, at an inserted position; and
a retractor lock in the channel that is movable between a release position and a lock position, wherein the lock is configured such that (1) when the lock is in the release position the end portion of the first connector structure can be inserted into the channel to the inserted position and removed from the channel, and (2) when the lock is in the lock position the lock engages at least the first leg to resist withdrawal of the end portion of the first connector structure from the channel.

30. The component of claim 29 wherein the lock includes a cam that is rotatably mounted in the channel and that rotates between the release and lock positions.

31. The component of claim 30 wherein:
the channel includes a side wall; and
wherein when the cam is in the lock position the cam urges the first leg into engagement with the side wall of the channel.

* * * * *